United States Patent [19]

Dugar

[11] Patent Number: 5,321,031
[45] Date of Patent: Jun. 14, 1994

[54] 1,2-DISUBSTITUTED ETHYL AMIDES AS INHIBITORS OF ACAT

[75] Inventor: Sundeep Dugar, Bridgewater, N.J.

[73] Assignee: Schering Corporation, Kenilworth, N.J.

[21] Appl. No.: 950,379

[22] Filed: Sep. 23, 1992

[51] Int. Cl.$^5$ .................. A61K 31/44; C07D 221/20; C07D 241/04; C07C 233/01

[52] U.S. Cl. .................. 514/278; 514/237.8; 514/255; 514/327; 514/328; 514/329; 514/331; 514/617; 514/627; 544/168; 544/389; 544/390; 544/391; 546/16; 546/19; 546/220; 546/221; 546/222; 546/223; 546/224; 546/233; 546/234; 564/181; 564/207

[58] Field of Search .............. 544/168, 389, 390, 391; 546/16, 19, 220, 221, 222, 223, 224, 233, 234; 564/181, 207; 514/255, 237.8, 278, 327, 328, 329, 331, 617, 627

[56] References Cited

U.S. PATENT DOCUMENTS

| | | | |
|---|---|---|---|
| 3,784,577 | 1/1974 | Fukumaru et al. | 554/35 |
| 4,248,893 | 2/1981 | Kathawala et al. | 564/188 |
| 4,251,438 | 2/1981 | Moon | 544/373 |
| 4,420,475 | 12/1983 | Damon, II | 548/406 |
| 4,434,161 | 2/1984 | Barcza | 548/406 |
| 4,456,619 | 6/1984 | Kathawala | 514/627 |
| 4,518,789 | 5/1985 | Yu et al. | 514/534 |
| 4,603,145 | 7/1986 | DeVries et al. | 514/539 |
| 4,611,063 | 9/1986 | Damon, II | 548/406 |
| 4,716,175 | 12/1987 | Hoefle et al. | 514/357 |
| 5,149,709 | 9/1992 | Clader et al. | 514/486 |

FOREIGN PATENT DOCUMENTS 25569 3/1981 European Pat. Off. .

OTHER PUBLICATIONS

Nishida et al "Purpactins, New Inhibitor of ACAT" Biological Abs. 91:129161 (1991).

DeVries et al "Potential Antiatherosclerotic Agents" J. Med. Chem. 32 2318-25 (1989).

Primary Examiner—C. Warren Ivy
Assistant Examiner—Celia Chang
Attorney, Agent, or Firm—Paul A. Thompson; Anita W. Magatti

[57] ABSTRACT

Amides of the formula

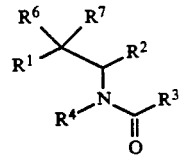

wherein:

$R^1$ is A and $R^2$ is B; $R^1$ is B and $R^2$ is A; or $R^1$ and $R^2$ are independently selected from the group B;

A is phenyl, substituted phenyl, heteroaryl, or substituted heteroaryl;

B is cycloalkyl, substituted cycloalkyl, heterocycloalkyl, or substituted heterocycloalkyl;

$R^3$ is an alkyl chain of 1 to 25 carbon atoms, branched or straight; an alkenyl chain of 2 to 25 carbon atoms, branched or straight; a substituted alkyl chain; a substituted alkenyl chain; an interrupted alkyl chain; an interrupted alkenyl chain; a substituted interrupted alkyl chain; or a substituted interrupted alkenyl chain;

$R^4$ is hydrogen, lower alkyl, phenyl, Q-substituted phenyl, heteroaryl or Q-substituted heteroaryl;

$R^6$ and $R^7$ are both H, or $R^6$ and $R^7$ together represent =O;

or a pharmaceutically acceptable salt thereof;

useful as inhibitors of acyl-coenzyme A:cholesterol acyl transferase and therefore in the treatment of atherosclerosis are disclosed.

6 Claims, No Drawings

1,2-DISUBSTITUTED ETHYL AMIDES AS INHIBITORS OF ACAT

BACKGROUND OF THE INVENTION

The present invention relates to 1,2-disubstituted ethyl amides useful in the treatment and prevention of atherosclerosis.

Atherosclerotic coronary heart disease represents the major cause for death and cardiovascular morbidity in the western world. Risk factors for atherosclerotic coronary heart disease include hypertension, diabetes mellitus, family history, male sex, cigarette smoking and serum cholesterol. A total cholesterol level in excess of 225–250 mg/dl is associated with significant elevation of risk.

Cholesterol esters are a major component of atherosclerotic lesions and the major storage form of cholesterol in arterial wall cells. Formation of cholesterol esters is also a key step in the intestinal absorption of dietary cholesterol. The intracellular esterification of cholesterol is catalyzed by the enzyme acyl CoA:-cholesterol acyl transferase (ACAT, EC 2.3.1.26). Thus, inhibition of ACAT is likely to inhibit the progression of atherosclerotic lesion formation, decrease the accumulation of cholesterol esters in the arterial wall, and block the intestinal absorption of dietary cholesterol.

A number of amides have been reported as being useful in lowering cholesterol and/or in inhibiting the formation of cholesterol-containing lesions in mammalian arterial walls. U.S. Pat. No. 3,784,577 to Fukurmaru et al discloses fatty acid amide derivatives of the formula R-CONHR$^1$ wherein RCO is a fatty acid radical and R$^1$ is 1-α-benzylbenzyl.

U.S. Pat. No. 4,603,145 to De Vries et al discloses diaryl alkanamides of the formula

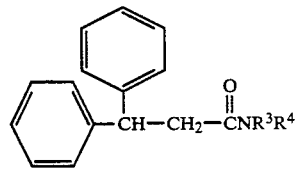

wherein R$^3$ and R$^4$ independently include benzyl and phenethyl.

U.S. Pat. No. 4,420,475 to Damon et al discloses silicon-bearing amides of the formula

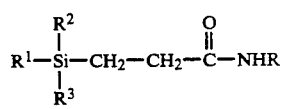

wherein R$^1$, R$^2$ and R$^3$ independently can be alkyl, phenyl, benzyl or phenethyl and R can be 1-α-benzylbenzyl optionally substituted in the phenyl rings. U.S. Pat. No. 4,434,161 to Barcza discloses similar compounds having a sulfur atom in the chain between the silicon atom and the carbonyl group.

U.S. Pat. No. 4,456,619 to Kathawala discloses amides of 2-alkynoic acids of the formula

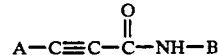

wherein A is alkyl, alkenyl or cyclopropanyl-substituted alkyl and B can be 1-α-benzylbenzyl, optionally substituted in the phenyl rings.

U.S. Pat. No. 4,716,175 to Hoefle et al discloses fatty acid amides of the formula

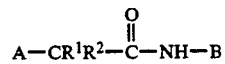

wherein A is an alkyl chain, R$^1$ and R$^2$ can each be phenylmethyl, and B can be phenyl, benzyl, pyrimidinyl or pyridyl.

U.S. Pat. No. 4,518,789 to Yu et al discloses dermatologically useful phenyl alpha-acyloxyacetamides of the formula

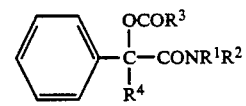

wherein R$^1$ and R$^2$ can be hydrogen, alkyl or aralkyl and R$^3$ and R$^4$ can be hydrogen, alkyl, aralkyl or aryl.

While some of these diphenylethylamides have shown in vitro ACAT inhibitory activity, none have been reported to show significant activity in whole animal models of atherosclerosis.

In addition, U.S. Pat. No. 5,149,709 discloses compounds, having in vivo anti-atherosclerotic activity, of the formula

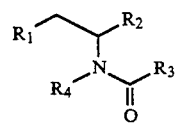

wherein R$_1$ and R$_2$ are independently a heteroaryl group selected from the group consisting of pyridinyl, pyrimidinyl, pyrazinyl, quinolyl, triazinyl, imidazolyl, thiophenyl, oxazolyl and furanyl; X-substituted heteroaryl wherein X is 1 to 3 substituents independently selected from the group consisting of halogeno, lower alkyl, hydroxy, lower alkoxy, amino, lower alkylamino, lower dialkylamino, acetamido, methanesulfonyl-amino, 2-(trimethylsilyl)ethoxymethyl, carboxy and lower alkoxycarbonyl; X-substituted phenyl; or N-substituted triazinyl or N-substituted imidazolyl wherein the N-substituents are selected from the group consisting of lower alkyl, 2-(trimethylsilyl)ethoxymethyl and R$_5$CO— wherein R is lower alkyl, phenyl, benzyl or 2,2-dimethylpropyl;

and in addition, one of R$_1$ and R$_2$ can be as defined above and the other can be phenyl;

R$_3$ is an alkyl chain of 1 to 25 carbon atoms, branched or straight, saturated or containing one or more double bonds; an alkyl chain as defined substituted by one or more substituents selected from the group consisting of phenyl, X-substituted phenyl, heteroaryl and X-substituted heteroaryl; an alkyl chain as defined interrupted by one or more groups independently selected from the group consisting of —O—, —S—, —SO—, —SO$_2$—, —NH—, —N(lower alkyl)—, —C(O)—, phenylene, X-substituted phenylene, heteroarylene and X-substituted heteroarylene; or an interrupted alkyl chain as defined substituted by one or more substituents selected from the group consisting of phenyl, X-substituted phenyl, heteroaryl and X-substituted heteroaryl;

R$_4$ is hydrogen, lower alkyl, phenyl, X-substituted phenyl, heteroaryl or X-substituted heteroaryl;

or a pharmaceutically acceptable salt thereof.

SUMMARY OF THE INVENTION

Novel compounds of the present invention which show significant in vivo atherosclerotic activity are represented by the formula

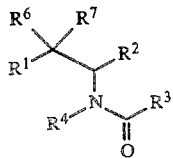

wherein:
R$^1$ is A and R$^2$ is B; R$^1$ is B and R$^2$ is A; or R$^1$ and R$^2$ are independently selected from the group B;

A is phenyl, Q-substituted phenyl, heteroaryl, or Q-substituted heteroaryl, wherein Q is 1 to 3 substituents independently selected from the group consisting of hydroxy, lower alkyl, lower alkoxy, halogeno, —COOH, —CONH$_2$, R$^8$O—C(O)—, R$^8$NH—C(O)—, (R$^8$)$_2$N—C(O)—, R$^8$NH—, (R$^8$)$_2$N— and R$^8$—C(O)—NH—, wherein R$^8$ is lower alkyl;

B is cycloalkyl, Y-substituted cycloalkyl, heterocycloalkyl, or Y-substituted heterocycloalkyl, wherein: Y is 1 to 3 substituents independently selected from the group consisting of alkyl, hydroxy, —COOH, —CONH$_2$, R$^8$O—C(O)—, R$^8$NH—C(O)—, (R$^8$)$_2$N—C(O)—, R$^5$O—, —S-(O)$_m$—R$^5$, —NH$_2$, R$^5$NH—, (R$^5$)$_2$N— and R$^5$—C-(O)—NH—, wherein m is 0, 1 or 2, R$^5$ is lower alkyl, phenyl or Q-substituted phenyl, and R$^8$ is as defined above; or Y is a bivalent group of the formula —O—(CH$_2$)$_2$—O—, or —(CH$_2$)$_4$—, wherein both termini of the bivalent group are attached to the same carbon atom, thereby constituting a spirofused substituent;

R$^3$ is an alkyl chain of 1 to 25 carbon atoms, branched or straight; an alkenyl chain of 2 to 25 carbon atoms, branched or straight; an alkyl or alkenyl chain as defined substituted by one or more substituents selected from the group consisting of phenyl, Q-substituted phenyl, phenoxy, heteroaryl and Q-substituted heteroaryl; and alkyl or alkenyl chain as defined interrupted by one or more groups independently selected from the group consisting of —O—, —S(O)$_m$—, —NH—, N(R$^5$)—, —C(O)—, phenylene, Q-substituted phenylene, heteroarylene and Q-substituted heteroarylene; or an interrupted alkyl chain or interrupted alkenyl chain as defined substituted by one or more substituents selected from the group consisting of phenyl, Q-substituted phenyl, heteroaryl and Q-substituted heteroaryl;

R$^4$ is hydrogen, lower alkyl, phenyl, Q-substituted phenyl, heteroaryl or Q-substituted heteroaryl;
R$^6$ and R$^7$ are both H, or R$^6$ and R$^7$ together represent =O;

or a pharmaceutically acceptable salt thereof.

Preferred are compounds of the formula I wherein R$^1$ is cycloalkyl, heterocycloalkyl or Y-substituted heterocycloalkyl; R$^2$ is phenyl or Q-substituted phenyl; and R$^4$, R$^6$ and R$^7$ are hydrogen.

Another group of preferred compounds of formula I is that wherein R$^1$ is phenyl, R$^2$ is cycloalkyl, and R$^4$, R$^6$ and R$^7$ are hydrogen.

Also preferred are compounds of formula I wherein R$^3$ is a diphenyl-substituted alkyl chain, a C$_{10}$–C$_{25}$ alkyl chain, a C$_{10}$–C$_{25}$ branched alkyl chain, a phenoxy-substituted C$_{10}$–C$_{25}$ alkyl chain or a C$_{10}$–C$_{25}$ alkenyl chain.

Yet another group of preferred compounds are compounds of formula I wherein R$^1$ is Y-substituted heterocycloalkyl, R$^2$ is phenyl or Q-substituted phenyl, R$^4$ is hydrogen and R$^6$ and R$^7$ together represent =O.

More preferred are compounds of the formula I wherein R$^1$ is cyclohexyl, morpholino, piperidinyl, piperidonyl, piperazinyl or Y-substituted heterocycloalkyl; R$^2$ is phenyl; and R$^4$, R$^6$ and R$^7$ are hydrogen.

Another group of more preferred compounds are those of the formula I wherein R$^3$ is diphenylmethyl, diphenylethyl, CH$_3$(CH$_2$)$_{14}$—, CH$_3$(CH$_2$)$_{16}$—, CH$_3$(CH$_2$)$_{12}$—, CH$_3$(CH$_2$)$_{10}$—, CH$_3$(CH$_2$)$_9$—C(CH$_3$)$_2$—, CH$_3$(CH$_2$)$_{11}$—C(CH$_3$)$_2$—, C$_6$H$_5$—O—(CH$_2$)$_{10}$—, CH$_3$(CH$_2$)$_{13}$—C(CH$_3$)$_2$—, CH$_3$(CH$_2$)$_7$CH=CH(CH$_2$)$_7$— or CH$_3$(CH$_2$)$_5$CH=CH(CH$_2$)$_7$—.

Most preferred are compounds of the formula I wherein R$^1$ is cyclohexyl, morpholino, piperidinyl, piperidonyl, piperazinyl or Y-substituted heterocycloalkyl; R$^2$ is phenyl; R$^3$ is diphenylmethyl, diphenylethyl, CH$_3$(CH$_2$)$_{14}$—, CH$_3$(CH$_2$)$_{16}$—, CH$_3$(CH$_2$)$_{12}$—, CH$_3$(CH$_2$)$_{10}$—, CH$_3$(CH$_2$)$_9$—C(CH$_3$)$_2$—, CH$_3$(CH$_2$)$_{11}$—C(CH$_3$)$_2$—, C$_6$H$_5$—O—(CH$_2$)$_{10}$—, CH$_3$(CH$_2$)$_{13}$—C(CH$_3$)$_2$—, CH$_3$(CH$_2$)$_7$CH=CH(CH$_2$)$_7$— or CH$_3$(CH$_2$)$_5$CH=CH(CH$_2$)$_7$—; and R$^4$, R$^6$ and R$^7$ are hydrogen; and compounds of the formula I wherein R$^1$ is Y-substituted heterocycloalkyl; R$^2$ is phenyl; R$^3$ is diphenylmethyl, diphenylethyl, CH$_3$(CH$_2$)$_{14}$—, CH$_3$(CH$_2$)$_{16}$—, CH$_3$(CH$_2$)$_{12}$—, CH$_3$(CH$_2$)$_{10}$—, CH$_3$(CH$_2$)$_9$— C(CH$_3$)$_2$—, CH$_3$(CH$_2$)$_{11}$—C(CH$_3$)$_2$—, C$_6$H$_5$—O—(CH$_2$)$_{10}$—, CH$_3$(CH$_2$)$_{13}$— C(CH$_3$)$_2$—, CH$_3$(CH$_2$)$_7$CH=CH(CH$_2$)$_7$— or CH$_3$(CH$_2$)$_5$CH=CH(CH$_2$)$_7$—; R$^4$ is hydrogen; and R$^6$ and R$^7$ together represent =O.

This invention also relates to the use of the ACAT inhibitors of the present invention as hypolipidemic and hypocholesterolemic agents in mammals.

In another aspect, the invention relates to pharmaceutical compositions comprising an ACAT inhibitor of the present invention in a pharmaceutically acceptable carrier.

DETAILED DESCRIPTION

As used herein, the term "lower alkyl" means straight or branched alkyl chains of 1 to 6 carbon atoms and "lower alkyoxy" similarly refers to alkoxy groups having 1 to 6 carbon atoms;

"halogeno" refers to fluorine, chlorine, bromine or iodine radicals;

"cycloalkyl" means a saturated carbocyclic ring having from 3 to 9, preferably from 3 to 6, carbon atoms;

"heterocycloalkyl" means a cycloalkyl group in which 1 to 3 ring members are heteroatoms selected from N, S and O, such as pyrrolidinyl, piperidinyl, morpholino, piperazinyl or piperidonyl;

"phenylene" means a bivalent phenyl group bound in an ortho, meta or para orientation;

"heteroaryl" means an aromatic group having from 2 to 14, preferably from 2 to 9, carbon atoms and from 1 to 3 heteroatoms, selected from O, N and S, such as pyridyl, furanyl, thienyl, thiazolyl, imidazolyl, pyrimidinyl, pyrazinyl, pyridazinyl, triazinyl, thiadizolyl, benzofuranyl, indolyl, benzothienyl, pyrazolyl or oxazolyl; and "heteroarylene" means a bivalent heteroaryl group.

Where $R^1$ or $R^2$ is a heteroaryl group containing a secondary amino group (e.g. triazinyl or imidazolyl), the $R_1$ or $R_2$ heteroaryl group can be attached to the rest of the molecule either by a ring carbon or by the secondary amino group (e.g. 1-imidazolyl or 2-imidazolyl).

The alkyl chain as defined in $R^3$ can be a radical of a synthetic or natural fatty acid, either saturated or containing one or more carbon to carbon double bonds, or can be an interrupted alkyl or alkenyl chain wherein one or more of the carbon atoms in the chain can be replaced by an —O—, —S—, —SO—, —SO$_2$—, —NH—, —N(lower alkyl)—, —C(O)—, phenylene or heteroarylene group. When substituted by optionally substituted phenyl or heteroaryl groups, the alkyl chain, alkenyl chain, interrupted alkyl chain or interrupted alkenyl chain may be independently substituted on different carbon atoms, di-substituted on one carbon atom, or both.

One skilled in the art will recognize that the number of double bonds present, the replacement of carbon atoms in the chain and the presence of substituents on the carbon atoms in the chain are all dependent on the length of the chain: shorter alkyl chains cannot accommodate as many carbon replacements or substituents as longer alkyl chains, and similarly, shorter alkenyl chains cannot accommodate as many double bonds, carbon replacements or substituents as longer alkenyl chains. In general, alkenyl chains contain 1 to 4 double bonds, conjugated or non-conjugated. Where carbon atoms are replaced, 1 to 4 replacement groups can be present. Similarly, when carbon atoms in the chain are substituted, 1 to 4 substituents can be present.

Examples of alkyl chains are as follows, wherein the group —C(O)R$^3$ represents a palmitoyl [i.e., CH$_3$(CH$_2$)$_{14}$C(=O)—], 2,2-dimethylpalmitoyl [i.e., CH$_3$(CH$_2$)$_{13}$—C(CH$_3$)$_2$—C(=O)—], caproyl [i.e., CH$_3$(CH$_2$)$_4$C(=O)—], myristoyl [i.e., CH$_3$(CH$_2$)$_{12}$C(=O)—], 2,2-dimethylmyristoyl [i.e., CH$_3$(CH$_2$)$_{11}$—C(CH$_3$)$_2$—C(=O)—], capryloyl [i.e., CH$_3$(CH$_2$)$_8$C(=O)—], stearoyl [i.e., CH$_3$(CH$_2$)$_{16}$C(=O)—], dodecanoyl [i.e., CH$_3$(CH$_2$)$_{10}$C(=O)—] or 2,2-dimethyl-dodecanoyl group [i.e., CH$_3$(CH$_2$)$_9$— C(CH$_3$)$_2$—C(=O)—].

Examples of alkenyl chains are as follows, wherein the group —C(O)R$^3$ represents oleoyl [i.e., (Z)—CH$_3$(CH$_2$)$_7$CH=CH(CH$_2$)$_7$— C(=O)—], 2,2-dimethyloleoyl [i.e., (Z)—CH$_3$(CH$_2$)$_7$CH=CH(CH$_2$)$_6$—C(CH$_3$)$_2$— —C(=O)—], palmitoleoyl [i.e., CH$_3$(CH$_2$)$_5$CH=CH(CH$_2$)$_7$—C(=O)—], linoleoyl [i.e., CH$_3$(CH$_2$)$_4$CH=CHCH$_2$CH=CH(CH$_2$)$_7$—C(=O)—], linolenoyl [i.e., CH$_3$(CH$_2$CH=CH)$_3$(CH$_2$)$_7$—C(=O)—], elaidoyl [i.e., (E)—CH$_3$(CH$_2$)$_7$CH=CH(CH$_2$)$_7$—C(=O)—], eicosatetraenoyl [i.e., CH$_3$(CH$_2$)$_4$(CH=CHCH$_2$)$_4$(CH$_2$)$_2$—C(=O)—], and eicosapentaenoyl [i.e., CH$_3$(CH$_2$CH=CH)$_5$(CH$_2$)$_3$—C(=O)—].

Examples of —C(O)R$^3$ groups wherein the carbon atoms are substituted are phenylacetyl and those having the formula —C(O)CH(C$_6$H$_4$Q)—(CH$_2$)$_n$—C$_6$H$_4$Q wherein Q is hydrogen or is as defined above and n is 0 to 10, for example diphenylacetyl, 2,2-diphenylpropanyl, and di-(4-chlorophenyl)acetyl or 2,3-diphenylpropanyl.

Examples of —C(O)R$^3$ groups wherein carbon atoms in the chain are replaced are: 3-methoxy-4-(tetradecyloxy)-benzoyl, 11-[N-(2,2-diphenylacetyl)amino]undecanoyl and phenoxyundecanoyl.

Compounds of the invention have at least one asymmetrical carbon atom and therefore include stereoisomers. The invention includes d and l isomers in both pure form and in admixture, including racemic mixtures. Isomers can be prepared using conventional techniques, either by reacting enantiomeric starting materials or by separating isomers of a compound of formula I.

Isomers may include geometric isomers, e.g. when R$^3$ contains a double bond, said double bond can occur as an E or Z isomer. All such isomers are contemplated for this invention.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

The following solvents and reagents employed in preparing compounds of the present invention are identified by the abbreviations indicated: diethyl ether (Et$_2$O); ethyl acetate (EtOAc); methanol (MeOH); ethanol (EtOH); tetrahydrofuran (THF); N,N-dimethylformamide (DMF); dicyclohexylcarbodiimide (DCC); 1-(dimethylaminopropyl)-3-ethylcarbodiimide hydrochloride (EDCl); dimethylaminopyridine (DMAP); diethylazodicarboxylate (DEAD); triphenylphosphine (TPP); trifluoroacetic anhydride (TFAA), p-toluenesulfonic acid (p-TSA); 1-hydroxybenzotriazole (HOBT).

Compounds of formula I can be prepared under standard reaction conditions well known in the art. For example, compounds of the formula I can be prepared by coupling an amine of the formula II with a carboxylic acid of the formula III in the presence of a coupling agent, such as DCC or EDCl, and a tertiary amine base, such as DMAP or triethylamine, in a suitable solvent, such as CH$_2$Cl$_2$.

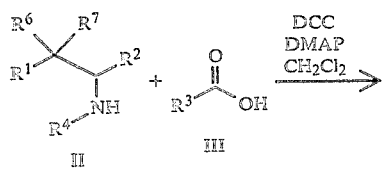

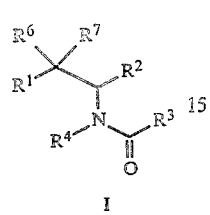

Alternatively, compounds of the formula I can be prepared by acylating an amine of the formula II with an acid halide, preferably an acid chloride, of the formula IV, in the presence of a tertiary amine base, such as triethylamine, in a suitable solvent, such as CH$_2$Cl$_2$.

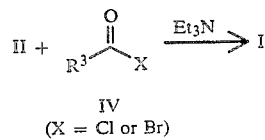

Amines of the formula II can be prepared by methods well known in the art. For example, amines of the formula IIa, e.g. an amine of the formula II wherein R$^4$, R$^6$ and R$^7$ are H, can be prepared from a ketone of the formula V by reacting the ketone with hydroxylamine hydrochloride to form an oxime of the formula VI, followed by hydrogenation in the presence of a suitable catalyst, such as palladium on carbon, preferably 10% Pd on carbon, and a suitable solvent, such as EtOAc or a lower alkyl alcohol, preferably MeOH or EtOH.

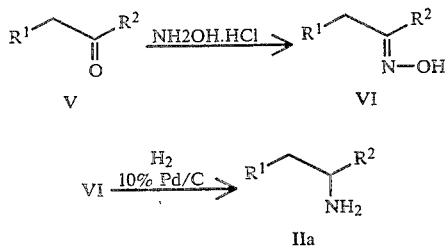

Alternatively, an amine of the formula IIb, e.g. an amine of the formula II wherein R$^4$ is H, can be prepared from an alcohol of the formula VII by treating with diphenylphosphoryl azide, DEAD and TPP, in a suitable solvent, such as THF, to form the azide VIII, which is hydrogenated in the presence of a suitable catalyst, such as palladium on carbon, preferably 10% Pd on carbon, and a suitable solvent, such as EtOAc or a lower alkyl alcohol, preferably MeOH or EtOH, to give the amine IIb.

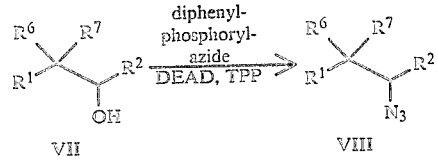

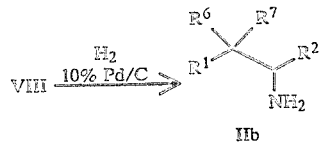

Amines of the formula II, wherein R$^4$ is lower alkyl, phenyl, Q-substituted phenyl, heteroaryl or Q-substituted heteroaryl, can be prepared by procedures well known in the art. Examples include: reacting an amine of the formula IIb with an alkylating agent, e.g. an alkyl halide, mesylate or triflate, in the presence of a suitable base; or for preparing an amine of formula II, wherein R$^6$ and R$^7$ are H, condensing a ketone of the formula V with an amine of the formula IX to form a Schiff's base, i.e. an imine of the formula X, followed by reduction, e.g. either by hydrogenation in the presence of a suitable catalyst, such as Pd or Pt, or treatment with a suitable reducing agent, such as LiAlH$_4$.

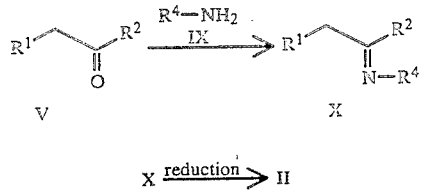

X $\xrightarrow{\text{reduction}}$ II

Ketones of the formula V and alcohols of the formula VII are either commercially available or can be prepared by procedures well known in the art. For example, ketones of the formula V, wherein R$^2$ is A can be prepared from an acid of the formula R$^1$CH$_2$COOH by converting the acid to an acid chloride of the formula R$^1$CH$_2$COCl, e.g. by treating with SOCl$_2$ or (COCl)$_2$, then reacting the acid chloride with a compound of the formula R$^2$H, wherein R$^2$ is A, in the presence of a suitable Lewis acid, e.g. AlCl$_3$.

Compounds of the formula Ia, i.e., compounds of the formula I wherein R$^1$ is heterocycloalkyl or Y-substituted heterocycloalkyl having a nitrogen atom at the position of attachment to the rest of the molecule, and R$^6$ and R$^7$ together represent =O, can be prepared by coupling a carboxylic acid of the formula XI with a compound of the formula R$^1$—H, wherein R$^1$ is heterocycloalkyl or Y-substituted heterocycloalkyl having a nitrogen atom at the position of attachment to the hydrogen atom. The coupling can be carried in the presence of: a coupling agent, e.g. EDCl or DCC; a tertiary amine base, e.g. triethylamine or N-methylmorpholine; an activating agent, such as HOBT; and a suitable solvent, such as DMF.

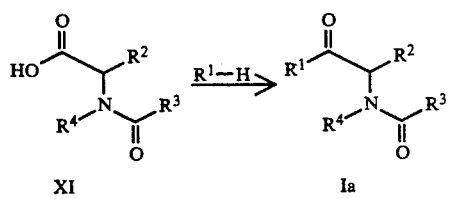

Compounds of the formula XI can be prepared by esterifying an amino acid of the formula XII, converting the resulting amino ester XIII to an amido ester XIV, e.g. by reacting with an acid halide of the formula IV, as defined above, in the presence of a tertiary amine base, followed by hydrolysis of the ester group of XIV, e.g. by treating with an aqueous base, such as NaOH in water.

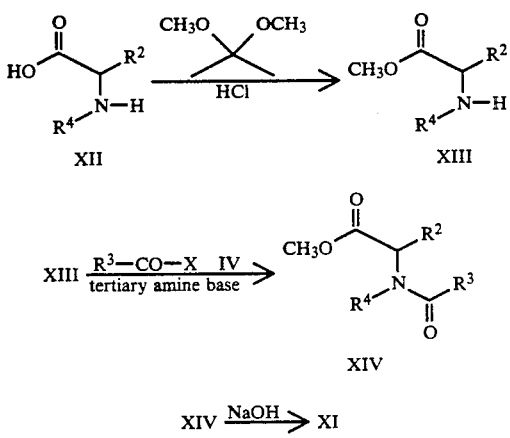

Amino acids of the formula XII are commercially available or can be prepared via procedures well known to those skilled in the art.

Reactive groups not involved in the above processes can be protected during the reactions with conventional protecting groups which can be removed by standard procedures after the reaction. The following table shows some typical protecting groups:

| Group to be protected | Protected Group |
|---|---|
| —COOH | —COOalkyl, —COObenzyl, —COOphenyl |
| ⟩NH | ⟩NCOalkyl, ⟩NCObenzyl, ⟩NCOpheny, |
| | ⟩NCH$_2$OCH$_2$CH$_2$Si(CH$_3$)$_3$, |
| | ⟩NC(=O)OC(CH$_3$)$_3$ |
| ⟩C=O | (cyclic acetals/ketals) |

| Group to be protected | Protected Group |
|---|---|
| —OH | —OCH$_3$ |
| —NH$_2$ |  (succinimidyl) |

We have found that the compounds of this invention are inhibitors of ACAT in vitro and in whole animal models the compounds have been found to significantly reduce the formation of liver cholesterol esters. Thus, compounds of this invention are hypocholesterolemic and hypolipidemic agents by virtue of their ability to inhibit the esterification and intestinal absorption of cholesterol; they are therefore useful in the treatment and prevention of atherosclerosis in mammals, in particular in humans.

In addition to the compound aspect, the present invention therefore also relates to a method of treating atherosclerosis, in particular by reducing serum cholesterol, which method comprises administering to a mammal in need of such treatment a hypocholesterolemic effective amount of a compound of this invention. The compound is preferably administered in a pharmaceutically acceptable carrier suitable for oral administration.

The in vitro and in vivo activity of the present compounds can be determined by the following procedures.

ACAT ASSAY (IN VITRO)

This assay measures the activity of ACAT by measuring the ACAT-mediated transfer of tritiated oleic acid from acyl-CoA to cholesterol to give labelled cholesterol oleate. Rat liver microsomes are used as the source of ACAT. Assays are performed in round bottom microtiterplates using a total incubation volume of 50 μL. Each incubation well receives 10 μL assay buffer (0.5M KHPO$_4$, 10 μM dithiothreitol, pH 7.4), 7.5 μL of 40 mg/mL BSA (Bovine Serum Albumin) and 12.5 μg of microsomal protein. The test compound (in sufficient amount to bring the final concentration to from 0.1 to 25 μM), reference compound, or vehicle control is added and the final volume brought to 47 μL. The microtiterplate is then floated on the surface of a 37° C. water bath for fifteen minutes. Incubations are started by the addition of 3 μL $^3$H-acyl CoA (1μ Ci/well, final concentration of 10 μM acyl CoA). The plate is then returned to the water bath for 15 minutes. The incubations are then terminated by application of 15 μL from each incubation to individual lanes on a thin layer plate (Silica Gel GF 20×20 cm). Standards are applied to several lanes so that the cholesterol ester band can be identified. After drying, the plates are eluted with 90:10:1 petroleum ether:diethyl ether:acetic acid. The standards are visualized via iodine vapor, and the regions corresponding to cholesterol ester are scraped into 7 mL scintillation vials. 4 mL of scintillant are added to each vial, and the radioactivity quantified. Background count is determined by the boiled controls. Full activity is determined by activity in the presence of vehicle. The percent inhibition is calculated by substracting the background from both and test samples, and the test value is calculated as a percentage of the control. For $IC_{50}$ determinations, the inhibition is plotted against drug does on a log scale and the concentration at which 50% inhibition is obtained is determined.

IN VIVO ASSAY OF HYPOLIPIDEMIC AGENTS USING THE HYPERLIPIDEMIC HAMSTER

Hamsters are separated into groups of six and given a control cholesterol diet (Purina Chow #5001 containing 0.5% cholesterol) for seven days. Diet consumption is monitored to determine dietary cholestrol exposure in the face of test compounds. The animals are dosed with the test compound once daily beginning with the initiation of diet. Dosing is by oral gavage of 0.2 mL of corn oil alone (control group) or solution (or suspension) of test compound in corn oil. All animals moribound or in poor physical condition are euthanized. After seven days, the animals are anesthetized by IM injection of ketamine and sacrificed by decapitation. Blood is collected into vacutainer tubes containing EDTA for plasma lipid analysis and the liver excised for tissue lipid analysis. Data is reported as percent reduction of lipid versus control.

The present invention also relates to a pharmaceutical composition comprising a compound of this invention and a pharmaceutically acceptable carrier. The compounds of formula I can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible filters, binders, disintegrants, buffers, preservatives, anti-oxidants, lubricants, flavorings, thickeners, coloring agents, emulsifiers and the like.

The daily hypocholesteremic or hypolipidemic dose of a compound of formula I is about 7 to about 30 mg/kg of body weight per day. For an average body weight of 70 kg, the dosage level is therefore from about 500 to about 2000 mg of drug per day, given in a single dose or 2-4 divided doses. The exact dose, however, is determined by the attending clinician and is dependent on the potency of the compound administered, the age, weight, condition and response of the patient.

Following are preparations of starting materials and examples of preparing compounds of formula I.

PREPARATION 1

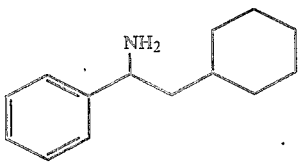

Step A:

Add 3 mL of oxalyl chloride to a solution of 1 g of cyclohexylacetic acid in 30 mL of benzene and heat the mixture at 60°-70° C. for 3 h. Remove the excess oxalyl chloride, and 10 mL of benzene, by fractional distillation. Cool the reaction mixture to 0° C., add 1.03 g of $AlCl_3$ and stir overnight while warming to room temperature. Pour the mixture into ice and concentrated HCl, then extract with EtOAc. Wash the EtOAc extract with saturated $NaHCO_3$ (aqueous), then with brine and concentrate to a residue. Chromatograph the residue (silica gel, 3:7 $CH_2Cl_2$/hexane) to give 1.35 g of the product

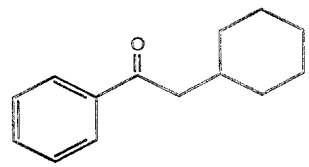

Step B:

Heat a mixture of 0.5 g of the product of Step A, 0.68 g of hydroxylamine hydrochloride, 15 mL of methanol and 15 mL of water at 60° C. overnight. Pour the mixture into water and extract with EtOAc. Concentrate the EtOAc extract to give 0.505 g of the product

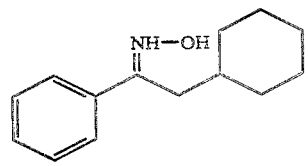

Step C:

The product of step B (0.505 g) in 20 mL of EtOH is hydrogenated over 10% Pd on carbon at 48 psi for 48 h. Filter and concentrate the filtrate to give 0.48 g of the title compound.

PREPARATION 2

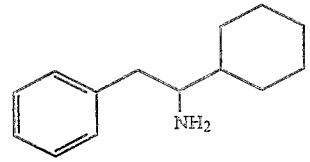

Step A:

Slowly add 15.6 mL of a 1M solution of benzylmagnesium bromide to a solution of 1 g of cyclohexane carboxaldehyde in 100 mL of $Et_2O$ at 0° C. Stir the mixture at 0° C. for 1 h., then stir for 1 h. more while warming to room temperature. Quench the mixture with 50 mL of saturated $NH_4Cl$ (aqueous), then add 50 mL of concentrated HCl. Wash the organic solution with saturated $NaHCO_3$ (aqueous), then concentrate to a residue. Chromatograph the residue (silica gel, $CH_2Cl_2$) to give 0.73 g of the product

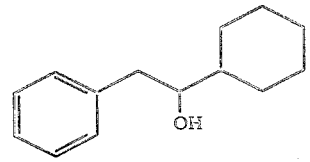

Step B:

Slowly add 1.22 g of diphenylphosphoryl azide to a solution of 0.73 g of the product of step A, 0.81 g of DEAD and 1.17 g of TPP in 50 mL of THF at 0° C. Stir the mixture for 16 h. while warming to room temperature. Concentrate to a residue and chromatograph the residue (silica gel, 25:75 CH$_2$Cl$_2$/hexane) to give 0.69 g of the product

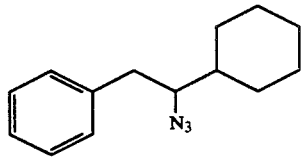

Step C:
Hydrogenate a solution of 0.59 g of the product of step B in 20 mL of MeOH and 5 mL of EtOAc over 10% Pd on carbon at 48 psi overnight. Filter and concentrate to give 0.5 g of the title compound.

PREPARATION 3

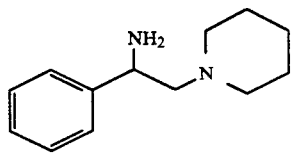

Step A:
Slowly add 20 g of α-bromoacetophenone to a solution of 25.6 g of piperidine in 300 mL of THF at 0° C., then stir for 18 h. while warming to room temperature. Remove the solvent in vacuo, dilute with saturated NaHCO$_3$ (aqueous) and extact with EtOAc. Concentrate the EtOAc extract to give 19.55 g of the product

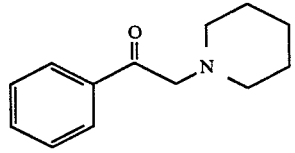

Step B:
Add 10 g of hydroxylamine hydrochloride to 19.55 g of the product of step A in 70 mL of pyridine at 0° C., then stir overnight while warming to room temperature. Pour the mixture into water and extract with EtOAc. Concentrate the EtOAc extract to a residue and chromatgraph the residue (silica gel, 7:3 EtOAc/hexane) to give 12.56 g of the product

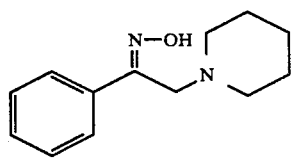

Step C:
Hydrogenate 10 g of the product of step B in 200 mL of EtOH over 10% Pd on carbon (1 g) at 47 psi overnight. Filter and concentrate the filtrate to give 8.74 g of the title compound.

PREPARATION 4

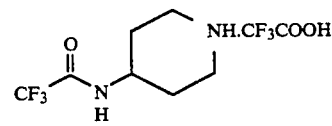

Step A:
Slowly add 25 mL of TFAA to 20 g of 4-amino-1-benzylpiperidine in 100 mL of CHCl$_3$ at 0° C. and stir overnight. Add 10 mL TFAA, heat the mixture at reflux for 2.5 h., then add another 10 mL of TFAA and heat at reflux for 2.5 h. more. Cool the mixture, filter, wash the solid with Et$_2$O and dry the solid to give 41.4 g of the product

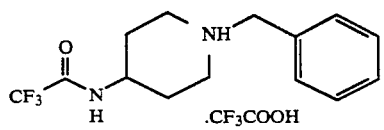

Step B:
Hydrogenate 20 g of the product of step A in EtOH over 2.5 g of 10% Pd on carbon at 58 psi overnight. Filter and concentrate the filtrate to a residue. Triturate the residue with Et$_2$O, then filter to give 9.87 g of the title compound.

PREPARATION 5

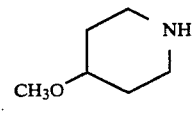

Step A:
Slowly add 25 mL of acetic anhydride to 25 g of 4-hydroxypiperidine in CH$_2$Cl$_2$. Stir the mixture at room temperature for 0.5 h. then heat at reflux until the mixture becomes homogeneous. Remove the solvent and distill the residue to give 13.8 g of the product

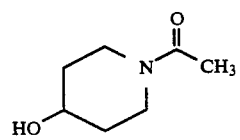

Step B:
Slowly add 3.2 g of 80% NaH in mineral oil to 13.8 g of the product of step A in 50 mL of DMF, stir the mixture for 1 h., then add 16.6 g of CH$_3$I and heat at 100° C. for 2.5 h, followed by stirring at room temperature overnight. Dilute the mixture with Et$_2$O, filter and concentrate the filtrate to a residue. Dissolve the residue in EtOAc, wash with a 3:1 mixture of saturated NaHCO$_3$/NaCl (aqueous), and concentrate the EtOAc solution to give 11.6 g of the product

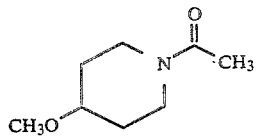

Step C:

Heat 11.6 g of the product of step B, 5.6 g of NaOH and 45 mL of water at reflux overnight. Cool the mixture, saturate with Na₂CO₃, extract with Et₂O and concentrate the extract to give 5.09 g of the title compound.

PREPARATION 6

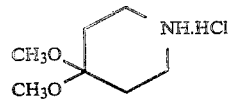

Add 370 mg of p-TSA to 3 g of 4-piperidone monohydrate hydrochloride and 12.8 mL of trimethylorthoformate in 20 mL of MeOH and heat the mixture at reflux for 4 h. Concentrate to a residue and triturate the residue with Et₂O. Filter and wash the solid with Et₂O to give 3.3 g of the title compound.

PREPARATION 7

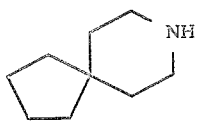

Slowly add a solution 25 g of 3,3-tetramethyleneglutarimide in 200 mL of Et₂O to a slurry of 17 g of LiAlH₄ and the mixture stirred at room temperature overnight, then heated at reflux for 3.5 h. Cool the mixture to 0° C., quench with Na₂SO₄.10 H₂O, filter and concentrate the filtrate to give 19.2 g of the title compound.

PREPARATION 8

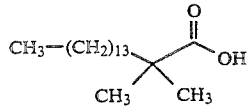

Slowly add 9.4 mL of diisopropylamine to a slurry of 2 g of 80% NaH in THF. Stir for 20 min. at room temperature, then add 6 g of isobutyric acid and heat the mixture at 60° C. for 30 min. Cool the mixture to 0°–10° C., then slowly add 42 mL of 1.6M n-butyllithium and stir for 2.5 h. while warming to room temperature. Add 18.7 g of bromotetradecane and stir overnight at room temperature. Remove the solvent under vacuum, pour the resulting residue into a mixture of concentrated HCl and ice, then extract with Et₂O. Concentrate the extract to a residue, which is chromatographed (silica gel, 5:5 CH₂Cl₂/MeOH) to give 9.3 g of the title compound.

EXAMPLE 1

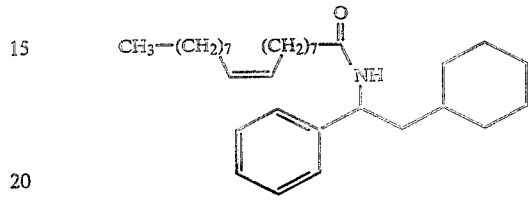

Add 140 mg of oleic acid in 3 mL of CH₂Cl₂ to a mixture of 100 mg of the product of Preparation 1, 112 mg of DCC, 6 mg of DMAP and 7 mL of CH₂Cl₂, and stir overnight at room temperature. Filter the mixture and concentrate to a residue, then chromatograph the residue (silica gel, 98:2 CH₂Cl₂/EtOAc) to give the title compound (185 mg), MS (M+1) 468.

EXAMPLE 2

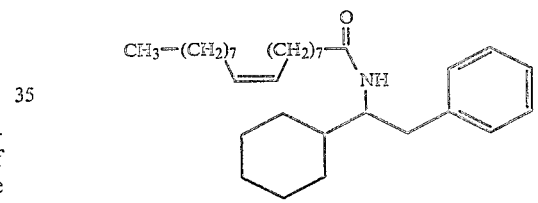

Add 325 mg of oleoyl chloride to a mixture of 200 mg of the product of Preparation 2, 164 mg of triethylamine and 10 mL of CH₂Cl₂ at 0° C. Stir for 1 h. at 0° C., then for 1 h. while warming to room temperature. Quench with 1N HCl, extract with CH₂Cl₂, concentrate to a residue and chromatograph the residue (silica gel, 98:2 CH₂Cl₂/EtOAc) to give 400 mg of the title compound, MS (M+1) 468.

Using the appropriate acid chloride and 1,2-di-substituted ethylamine, and substantially the same procedure, the following compounds can be prepared:

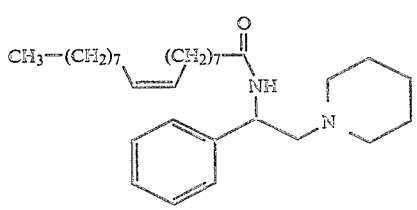

2A. MS (M + 1) 469

-continued
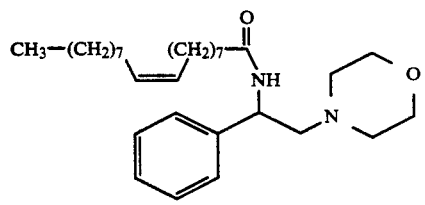
2B
MS (M + 1) 471
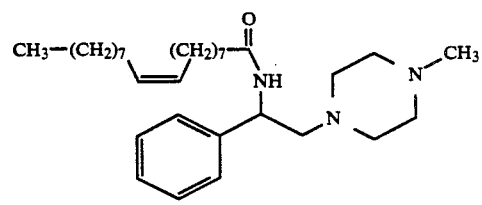
2C
MS (M + 1) 484
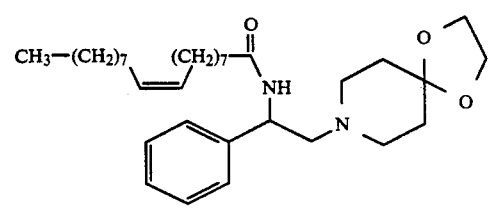
2D
MS (M + 1) 527
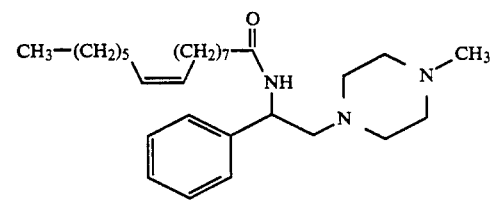
2E
MS (M + 1) 456
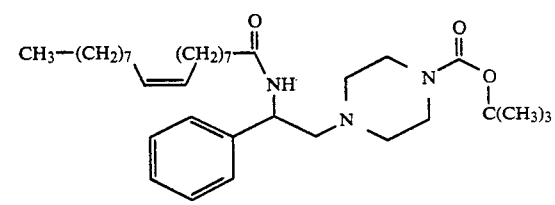
2F
MS (M + 1) 570
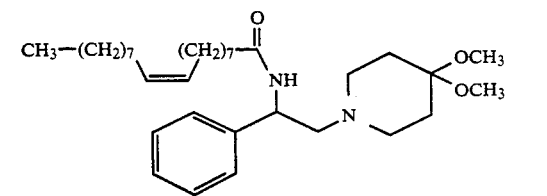
2G
MS (M + 1) 529
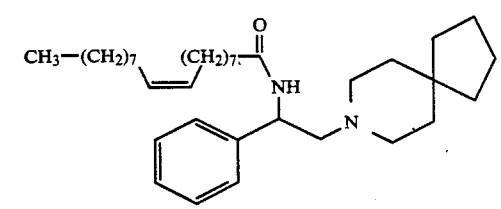
2H
MS (M + 1) 523
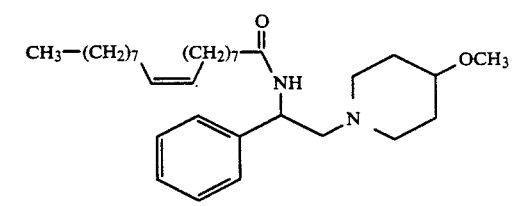
2J
MS (M + 1) 499

-continued
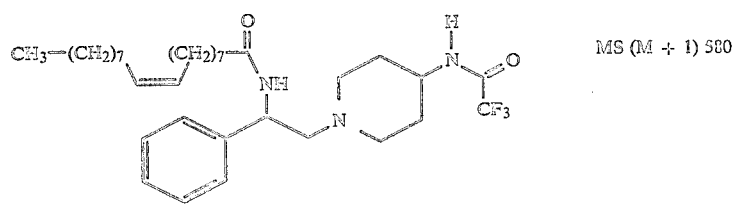 2K
MS (M + 1) 580
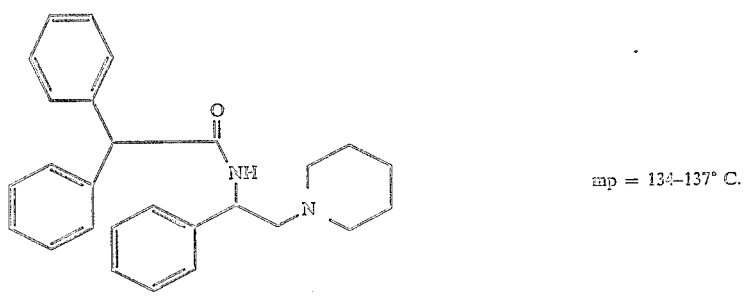 2L
mp = 134–137° C.
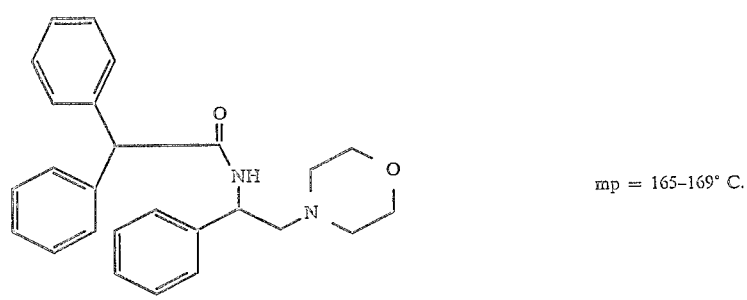 2M
mp = 165–169° C.
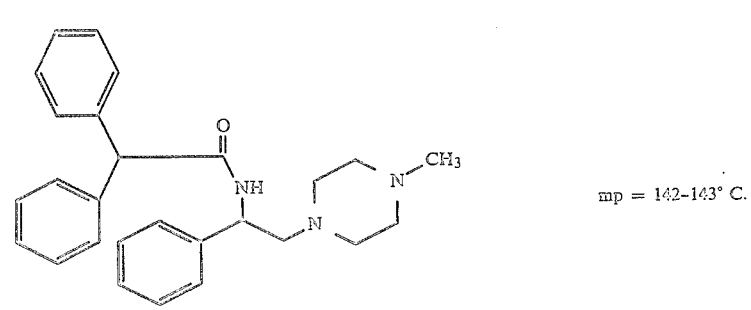 2N
mp = 142–143° C.
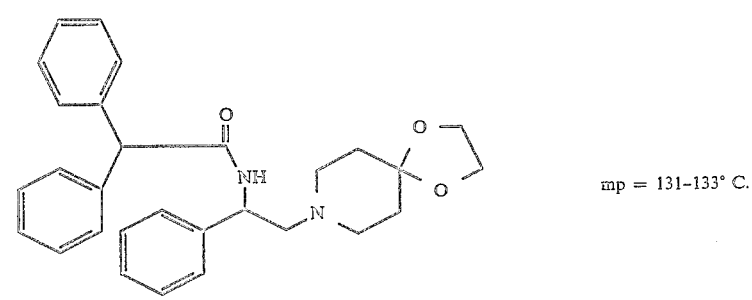 2P
mp = 131–133° C.

-continued
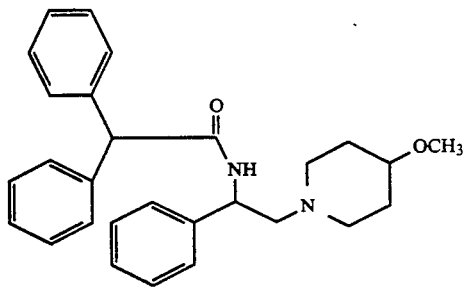
2Q
mp = 120–122° C.
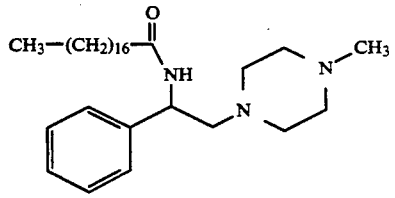
2R
mp = 77–78° C.
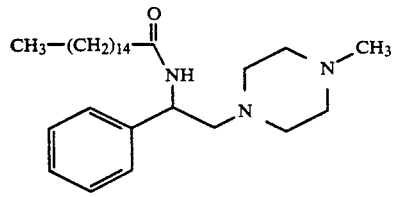
2S
MS (M + 1) 458
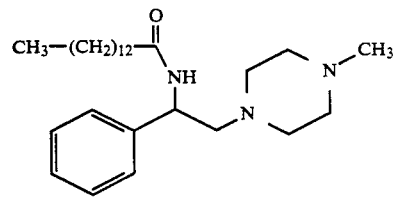
2T
MS (M + 1) 430
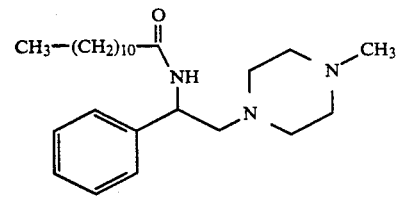
2U
mp = 64–67° C.
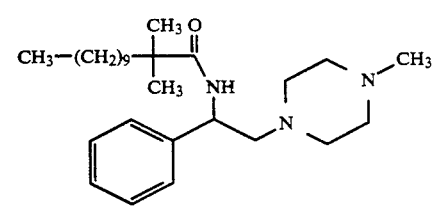
2V
MS (M + 1) 430
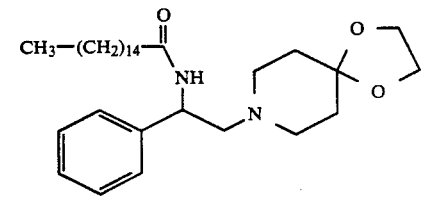
2W
MS (M + 1) 501

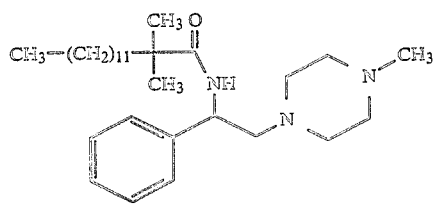

2X

MS (M + 1) 458

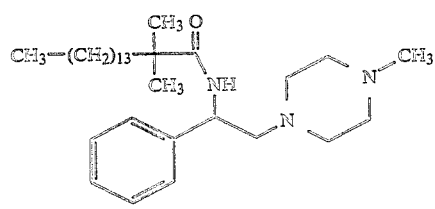

2Y

MS (M + 1) 486

EXAMPLE 3

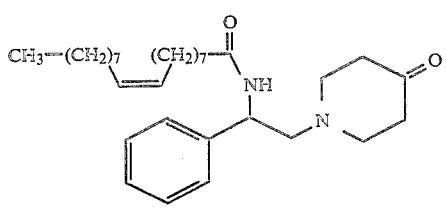

Add 6 mL of 3N HClO₄ to 500 mg of the product of Example 2G in 6 mL of THF and heat the mixture at 70° C. for 5.5 h. Pour the mixture into saturated NaHCO₃ (aqueous) and extract with EtOAc. Concentrate to a residue and chromatograph the residue (silica gel, 98:2 CH₂Cl₂/hexane) to give 350 mg of the title compound, MS (M+1) 483.

EXAMPLE 4

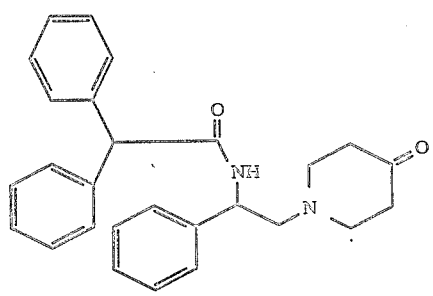

Add 6.1 g of the product of Example 2P to 110 mL of 85% H₂SO₄ at 0° C. and stir for 4.5 h. while warming warming to room temperature. Neutralize the mixture with NaHCO₃ and extract with EtOAc. Wash the EtOAc extract with water, then brine and concentrate to a residue. Recrystallize the residue from EtOAc/hexane to give 5.12 g of the title compound, m.p. 130°–131° C.

EXAMPLE 5

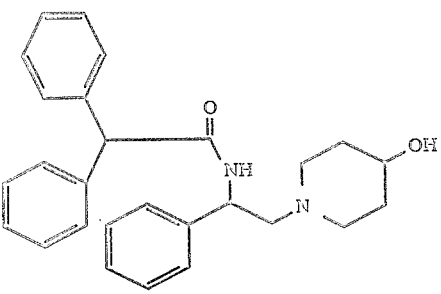

Add 125 mg of NaBH₄ to a mixture of 910 mg of the product of Example 4 in 50 mL of EtOH at 0° C. Stir overnight while warming to room temperature, then quench with water and extract with EtOAc. Concentrate to a residue and recrystallize the residue from Et₂O/hexane to give 904 mg of the title compound, MS (M+1) 415.

Using substantially the same procedure, the following compound can be prepared:

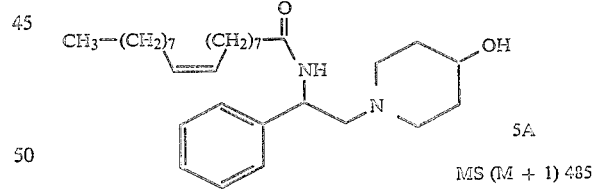

5A

MS (M + 1) 485

EXAMPLE 6

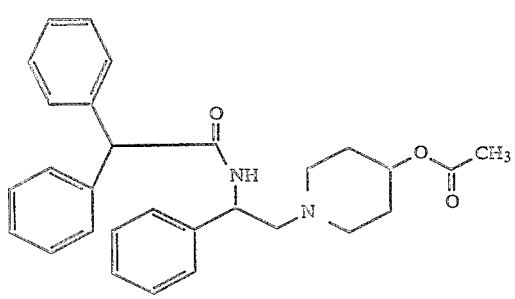

Add 114 mg of acetyl chloride to 400 mg of the product of Example 5 and 195 mg of triethylamine in 5 mL of THF at 0° C., and stir overnight while warming to room temperature. Dilute with water, neutralize with NaHCO₃ and extract with EtOAc. Concentrate the EtOAc extract to a residue and chromatograph the residue (silica gel, 97:3 CH₂Cl₂/MeOH) to give a mixture of the title compound and a second product. Separate the mixture by chromatography (silica gel pretreated with NaHCO₃, 4:6 EtOAc/hexane) to give 158 mg of the title compound, MS (M+1) 457, and 84 mg of a compound of the formula

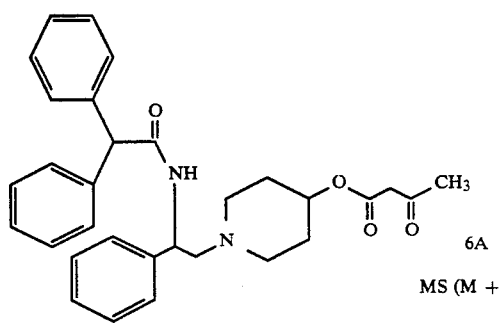

6A

MS (M + 1) 499

EXAMPLE 7

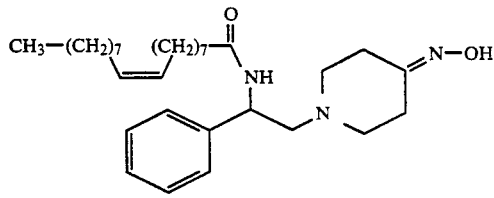

Add 90 mg of hydroxylamine hydrochloride to 315 mg of the product of Example 3, 215 mg of NaOAc and 3 mL of water in 15 mL of MeOH and heat at 70° C. overnight. Dilute the mixture with water, extract with EtOAc and concentrate the extract to a residue. Chromatograph the residue (silica gel, 96:4 EtOAc/MeOH) to give 250 mg of the title compound, MS (M+1) 498.

Using substantially the same procedure, the following compound can be prepared:

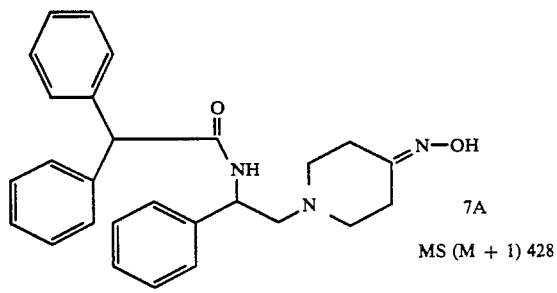

7A

MS (M + 1) 428

EXAMPLE 8

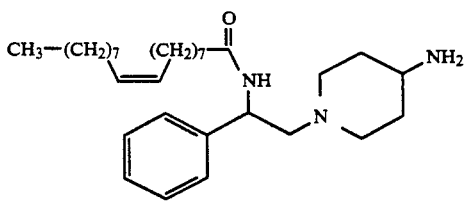

Add 3 mL of 7% K₂CO₃ (aqueous) to 500 mg of the product of Example 2K in 20 mL of MeOH and stir at room temperature for 3 days. Dilute the mixture with water, extract with EtOAc and concentrate the extract to give 413 mg of the title compound, MS (M+) 484.

EXAMPLE 9

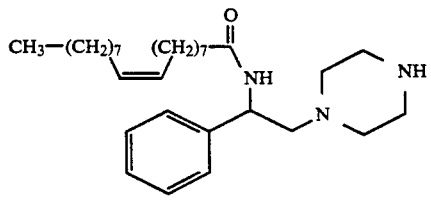

Stir a mixture of 1.03 g of the product of Example 2F and 15 mL of dioxane saturated with HCl gas at room temperature for 15 min., then pour the mixture into saturated NaHCO₃ (aqueous). Extract with EtOAc, concentrate the extract to a residue and chromatograph the residue (silica gel, 85:15 to 70:30 CH₂Cl₂/MeOH gradient) to give the title compound, MS (M+1) 470.

EXAMPLE 10

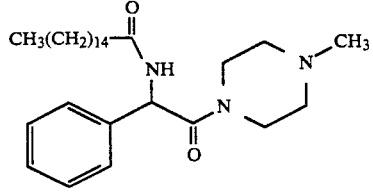

Step A:

Add 40 mL of concentrated HCl to a suspension of α-phenylglycine in 250 mL of 2,2-dimethoxypropane and stir at room temperature overnight. Remove the solvent under vacuum, keeping the temperature <60° C., then dissolve the residue in a solution of 20 mL of methane in 300 mL of anhydrous ether. Collect the resulting precipitate by filtration, suspend the precipitate in 50% NaHCO₃ (aqueous) and extract with CH₂Cl₂. Concentrate the extract to give 4.2 g of the product α-phenylglycine methyl ester.

Step B:

Add 3.3 g of palmitoyl chloride to a solution of 2 g of the product of Step A and 1.35 g of triethylamine in 100 mL of THF, then stir the mixture overnight. Pour the mixture into dilute HCl (aqueous) and collect the resulting precipitate by filtration. Wash the precipitate with water to give 4.66 g of the desired product

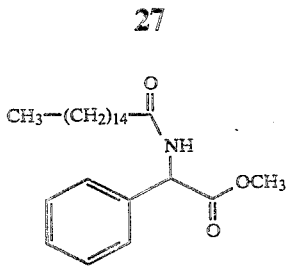

Step C:
Add 1 g of the product of Step B to a mixture of 12 mL of 1N NaOH (aqueous) and 60 mL of MeOH, then stir at room temperature overnight. Pour the mixture into ice and concentrated HCl, then extract with $CH_2Cl_2$. Concentrate the extract to give 0.5 g of the product

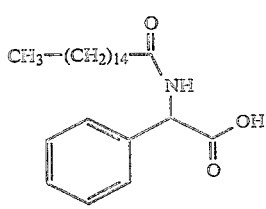

Step D:
Add N-methylpiperazine to a mixture of 0.5 g of the product of Step C, 0.19 g of HOBT, 0.143 g of N-methylmorpholine, 0.27 g of EDCl and 5 mL of DNF and stir at room temperature overnight. Pour the mixture into water and extract with EtOAc. Concentrate the extract to a residue and chromatograph (silica gel, 93:7 $CH_2Cl_2$/MeOH) to give 0.31 g of the title compound, mp=73°–75° C.

Using the appropriate amines and carboxylic acids, the following compounds can be prepared via the procedure of Example 10, Step D:

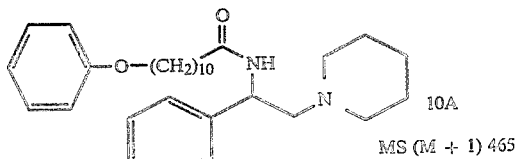

10A

MS (M + 1) 465

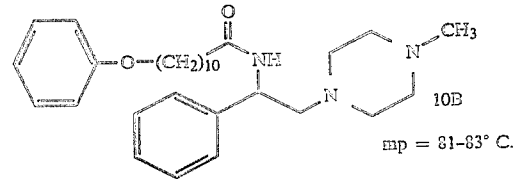

10B mp = 81–83° C.

Using the assay methods described above, the following data were obtained.

$$\begin{array}{c} R^6 \quad R^7 \\ \diagdown \diagup \\ R^1 \text{—} \overset{|}{\text{C}} \text{—} \overset{R^2}{\underset{HN}{\text{C}}} \text{—} \overset{R^3}{\underset{O}{\text{C}}} \end{array}$$

wherein

| $R^1$ | $R^2$ | $R^3$ | $R^6$ & $R^7$ | % ACAT Inhib. @ 10 μM | $IC_{50}$ (μM) | In Vivo 50 mpk % Redn. L/CE |
|---|---|---|---|---|---|---|
| cyclohexyl | $C_6H_5$— | (Z)—$CH_3(CH_2)_7CH\!=\!CH(CH_2)_7$— | H, H | 92 | 0.18 | — |
| $C_6H_5$— | cyclohexyl | (Z)—$CH_3(CH_2)_7CH\!=\!CH(CH_2)_7$— | H, H | 90 | 0.17 | 0 |
| morpholinyl | $C_6H_5$ | (Z)—$CH_3(CH_2)_7CH\!=\!CH(CH_2)_7$— | H, H | 99 | 0.3 | −21 |
| piperidinyl | $C_6H_5$ | (Z)—$CH_3(CH_2)_7CH\!=\!CH(CH_2)_7$— | H, H | 94 | 1.2 | −12 |
| N-methylpiperazinyl | $C_6H_5$ | (Z)—$CH_3(CH_2)_7CH\!=\!CH(CH_2)_7$— | H, H | 98 | 0.3 | −55 |

-continued

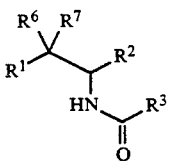

wherein

| R¹ | R² | R³ | R⁶ & R⁷ | % ACAT Inhib. @ 10 μM | IC₅₀ (μM) | In Vivo 50 mpk % Redn. L/CE |
|---|---|---|---|---|---|---|
| 1,4-dioxa-8-azaspiro[4.5]dec-8-yl | C₆H₅ | (Z)—CH₃(CH₂)₇CH=CH(CH₂)₇— | H, H | 93 | 0.01 | −35 |
| 4-oxopiperidin-1-yl | C₆H₅ | (Z)—CH₃(CH₂)₇CH=CH(CH₂)₇— | H, H | 100 | 0.18 | — |
| 4-(hydroxyimino)piperidin-1-yl | C₆H₅ | (Z)—CH₃(CH₂)₇CH=CH(CH₂)₇— | H, H | 100 | 0.03 | −21 |
| 4-methylpiperazin-1-yl | C₆H₅ | CH₃(CH₂)₅CH=CH(CH₂)₇— | H, H | 97 | 0.16 | −37 |
| 4-hydroxypiperidin-1-yl | C₆H₅— | (Z)—CH₃(CH₂)₇CH=CH(CH₂)₇— | H, H | 98 | 0.34 | −25 |
| 4-(tert-butoxycarbonyl)piperazin-1-yl | C₆H₅— | (Z)—CH₃(CH₂)₇CH=CH(CH₂)₇— | H, H | 100 | 0.06 | −22 |
| 4,4-dimethoxypiperidin-1-yl | C₆H₅— | (Z)—CH₃(CH₂)₇CH=CH(CH₂)₇— | H, H | 93 | 0.5 | −18 |
| 2-azaspiro[4.5]dec-2-yl (cyclopentane spiro piperidine) | C₆H₅— | (Z)—CH₃(CH₂)₇CH=CH(CH₂)₇— | H, H | 59 | — | 0 |
| 4-methoxypiperidin-1-yl | C₆H₅— | (Z)—CH₃(CH₂)₇CH=CH(CH₂)₇— | H, H | 93 | 0.15 | −24 |

-continued

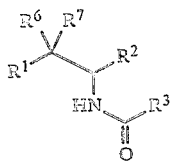

wherein

| R¹ | R² | R³ | R⁶ & R⁷ | % ACAT Inhib. @ 10 μM | IC$_{50}$ (μM) | In Vivo 50 mpk % Redn. L/CE |
|---|---|---|---|---|---|---|
| piperazinyl (HN-) | $C_6H_5-$ | (Z)—$CH_3(CH_2)_7CH=CH(CH_2)_7-$ | H, H | 64 | — | −54 |
| 4-(trifluoroacetamido)piperidinyl (CF$_3$CONH-) | $C_6H_5-$ | (Z)—$CH_3(CH_2)_7CH=CH(CH_2)_7-$ | H, H | 90 | 0.8 | 0 |
| 4-aminopiperidinyl ($H_2N-$) | $C_6H_5-$ | (Z)—$CH_3(CH_2)_7CH=CH(CH_2)_7-$ | H, H | ~90 | — | −59 |
| piperidinyl | $C_6H_5-$ | $C_6H_5-CH(C_6H_5)-$ | H, H | 64 | — | 0 |
| morpholinyl | $C_6H_5-$ | $C_6H_5-CH(C_6H_5)-$ | H, H | 94 | 3.0 | −15 |
| 4-methylpiperazinyl ($CH_3-$) | $C_6H_5-$ | $C_6H_5-CH(C_6H_5)-$ | H, H | 71 | 4.5 | −39 |
| 1,4-dioxa-8-azaspiro[4.5]decyl | $C_6H_5-$ | $C_6H_5-CH(C_6H_5)-$ | H, H | 94 | 0.3 | −26 |
| 4-oxopiperidinyl | $C_6H_5-$ | $C_6H_5-CH(C_6H_5)-$ | H, H | 90 | 0.5 | 0 |
| 4-hydroxypiperidinyl (HO-) | $C_6H_5-$ | $C_6H_5-CH(C_6H_5)-$ | H, H | 83 | 3.0 | −25 |
| 4-(hydroxyimino)piperidinyl (HON=) | $C_6H_5-$ | $C_6H_5-CH(C_6H_5)-$ | H, H | 94 | 0.4 | 0 |

5,321,031

-continued

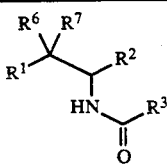

wherein

| R¹ | R² | R³ | R⁶ & R⁷ | % ACAT Inhib. @ 10 μM | IC$_{50}$ (μM) | In Vivo 50 mpk % Redn. L/CE |
|---|---|---|---|---|---|---|
| 4-(CH₃C(O)O)-piperidinyl (N-linked) | C₆H₅— | C₆H₅—CH(C₆H₅)— | H, H | 59 | — | —25 |
| 4-(AcAcO)-piperidinyl (N-linked); AcAc = CH₃C(O)CH₂C(O)— | C₆H₅— | C₆H₅—CH(C₆H₅)— | H, H | 53 | — | — |
| 4-(CH₃O)-piperidinyl (N-linked) | C₆H₅— | C₆H₅—CH(C₆H₅)— | H, H | 88 | 1.0 | —30 |
| 4-methylpiperazinyl (N-linked) | C₆H₅— | CH₃(CH₂)₁₆— | H, H | 90 | 0.5 | —25 |
| 4-methylpiperazinyl (N-linked) | C₆H₅— | CH₃(CH₂)₁₄— | H, H | 87 | 1.2 | —60 |
| 4-methylpiperazinyl (N-linked) | C₆H₅— | CH₃(CH₂)₁₂— | H, H | 81 | 7.0 | 0 |
| 4-methylpiperazinyl (N-linked) | C₆H₅— | CH₃(CH₂)₁₀— | H, H | 58 | — | 0 |
| 4-methylpiperazinyl (N-linked) | C₆H₅— | CH₃(CH₂)₉—C(CH₃)₂— | H, H | 94 | 0.39 | 0 |
| 1,4-dioxa-8-azaspiro[4.5]decan-8-yl | C₆H₅— | CH₃(CH₂)₁₄— | H, H | 99 | 0.16 | —19 |
| 4-methylpiperazinyl (N-linked) | C₆H₅— | CH(CH₂)₁₁—C(CH₃)₂— | H, H | 95 | 0.29 | —44 |

-continued

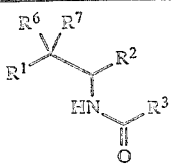

wherein

| $R^1$ | $R^2$ | $R^3$ | $R^6$ & $R^7$ | % ACAT Inhib. @ 10 μM | $IC_{50}$ (μM) | In Vivo 50 mpk % Redn. L/CE |
|---|---|---|---|---|---|---|
| [N-methylpiperazinyl] | $C_6H_5$— | $CH(CH_2)_{13}$—$C(CH_3)_2$— | H, H | 97 | 1.1 | −40 |
| [piperidinyl] | $C_6H_5$— | $C_6H_5$—O—$(CH_2)_{10}$— | H, H | 84 | 5.0 | 0 |
| [N-methylpiperazinyl] | $C_6H_5$— | $C_6H_5$—O—$(CH_2)_{10}$— | H, H | 80 | 4.0 | 0 |
| [N-methylpiperazinyl] | $C_6H_5$— | $CH_3(CH_2)_{14}$— | =O | 95 | 1.8 | −17 |

The following formulations exemplify some of the dosage forms of this invention. In each the term "active compound" designates a compound of formula I, preferably. However, this compound may be replaced by an equally effective amount of other compounds of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|   | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

I claim:

1. A compound of the formula

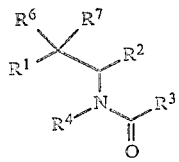

wherein:
 $R^1$ is B and $R^2$ is A;
 A is phenyl;

B is heterocycloalkyl, or Y-substituted heterocycloalkyl, wherein: heterocycloalkyl is piperidinyl; and Y is 1 to 3 substituents independently selected from the group consisting of hydroxy, HO—N=, $CH_3C(O)CH_2C(O)O$—, $CH_3C(O)O$—, $R^5O$— and —$NH_2$, wherein $R^5$ is lower alkyl; or Y is a bivalent group of the formula —O—$(CH_2)_2$—O— wherein both termini of the bivalent group are attached to the same carbon atom, thereby constituting a spirofused substituent;

$R^3$ is an alkyl chain of 1 to 25 carbon atoms, branched or straight; an alkenyl chain of 2 to 25 carbon atoms, branched or straight; or an alkyl or alkenyl chain as defined substituted by one or two substituents selected from the group consisting of phenyl or phenoxy;

$R^4$ is hydrogen;

$R^6$ and $R^7$ are both H;

or a pharmaceutically acceptable salt thereof.

2. A compound of claim 1 wherein —C(=O)—$R^3$ is palmitoyl, 2,2-dimethyl palmitoyl, caproyl, myristoyl, 2,2-dimethylmyristoyl, capryloyl, stearoyl, dodecanoyl, 2,2-dimethyl-dodecanoyl, oleoyl, 2,2-dimethyloleoyl, palmitoleoyl, linoleoyl, linolenoyl, elaidoyl, eicosatetraenoyl, eicosapentanenoyl, phenylacetyl, diphenylacetyl, 2,2-diphenyl-propanoyl, 2,3-diphenylpropanyl, or phenoxyundecanoyl.

3. A compound of claim 3 wherein $R^3$ is diphenylmethyl diphenylethyl, $CH_3(CH_2)_{14}$—, $CH_3(CH_2)_{16}$—, $CH_3(CH_2)_{12}$—, $CH_3(CH_2)_{10}$—, $CH_3(CH_2)_9$—$C(CH_3)_2$—, $CH_3(CH_2)_{11}$—$C(CH_3)_2$—, $C_6H_5$—O—$(CH_2)_{10}$—, $CH_3(CH_2)_{13}$—$C(CH_3)_2$—, $CH_3(CH_2)_7CH=CH(CH_2)_7$— or $CH_3(CH_2)_5CH=CH(CH_2)_7$—.

4. A compound of claim 1 represented by the formula:

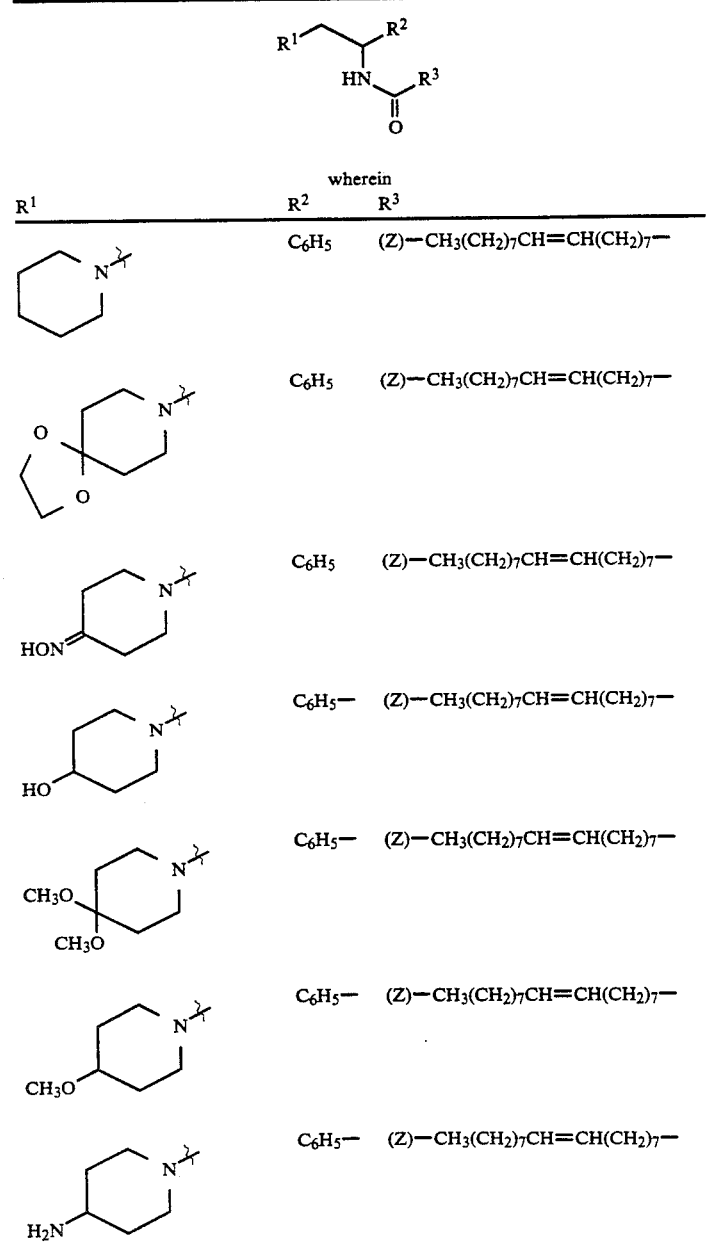

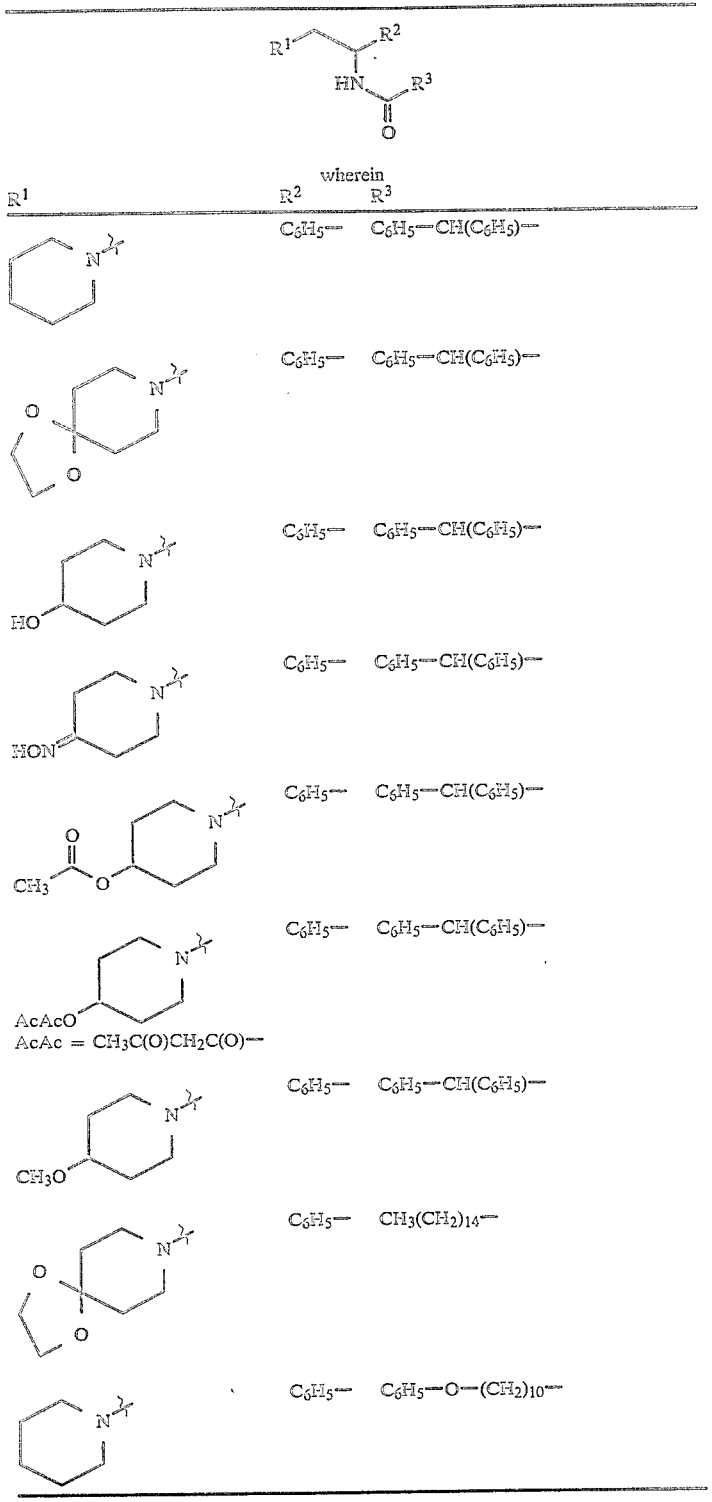
5. A pharmaceutical composition useful for treating atherosclerosis comprising an ACAT-inhibitory effective amount of a compound of claim 1 in a pharmaceutically effective carrier.
6. A method of treating atherosclerosis comprising administering to a mammal in need of such treatment a pharmaceutical composition of claim 5.
* * * * *

UNITED STATES PATENT AND TRADEMARK OFFICE
CERTIFICATE OF CORRECTION

PATENT NO. : 5,321,031
DATED      : JUNE 14, 1994
INVENTOR(S) : SUNDEEP DUGAR

It is certified that error appears in the above-identified patent and that said Letters Patent is hereby corrected as shown below:

IN CLAIM 6 AT COLUMN 40, LINE 62 BEFORE "ADMINISTERING" INSERT THE TERM --ORALLY--.

Signed and Sealed this

Eighth Day of November, 1994

Attest:

BRUCE LEHMAN

*Attesting Officer*      *Commissioner of Patents and Trademarks*